United States Patent [19]

Zappia et al.

[11] Patent Number: 4,883,670

[45] Date of Patent: Nov. 28, 1989

[54] COSMETIC PREPARATIONS CONTAINING UBIDECARENONES

[75] Inventors: Vincenzo Zappia; Mario De Rosa, both of Naples, Italy

[73] Assignee: Arval S.p.A., Milan, Italy

[21] Appl. No.: 222,914

[22] PCT Filed: Oct. 19, 1987

[86] PCT No.: PCT/EP87/00614

§ 371 Date: Jun. 20, 1988

§ 102(e) Date: Jun. 20, 1988

[87] PCT Pub. No.: WO88/03015

PCT Pub. Date: May 5, 1988

[30] Foreign Application Priority Data

Oct. 23, 1986 [IT] Italy ................................ 22105 A/86
Sep. 10, 1987 [IT] Italy ................................ 48373 A/87

[51] Int. Cl.$^4$ .............................................. A61K 37/22

[52] U.S. Cl. ..................... 424/450; 424/941; 424/449

[58] Field of Search ....................... 424/450, 94.1, 449

[56] References Cited

U.S. PATENT DOCUMENTS

| 4,325,942 | 4/1982 | Taki et al. | 424/94.1 |
| 4,617,187 | 10/1986 | Okuyama et al. | 424/94.1 |
| 4,636,381 | 1/1987 | Takeda et al. | 424/450 |
| 4,695,465 | 9/1987 | Kigasawa et al. | 424/94.1 |
| 4,767,624 | 8/1988 | Okuyama et al. | 424/94.1 |

*Primary Examiner*—Thurman K. Page
*Assistant Examiner*—P. L. Prater
*Attorney, Agent, or Firm*—Walter H. Schneider

[57] ABSTRACT

Ubidecarenones are effectively dissolved in an aqueous medium using N-acyl-2 amino-ethanesulphonates in which the acyl residue has more than 5 carbon atoms. Cosmetic compositions containing ubidecarenones so solubilized are effective in anti-aging and hydrating treatment.

6 Claims, No Drawings

COSMETIC PREPARATIONS CONTAINING UBIDECARENONES

The present invention relates to cosmetic preparations containing soluble ubidecarenones prepared by dispersing in aqueous media mixtures having different ratios of ubidecarenones and acyl derivatives of 2-amino-ethansulphonic acid.

The ubidecarenones form an important class of liposoluble vitaminic principles, particularly 2,3-dimethoxy-5-methyl-6-decaprenyl-1,4-benzoquinone, known as ubidecarenone-10, localized at the mitochondrial level, plays a key-role in mammals in the electron-transfer system and more generally in the energy production.

Because of said important metabolic roles, the ubiquinone-10 is widely used in a large number of cardiac pathologies, protecting the myocardium from ischemic phenomena and preserving the functions thereof.

Moreover, because of the ability of ubidecarenone-10 of influencing both the tissutal respiration and the peroxidative phenomena of the cellular membranes, said vitamin is particularly interesting for the prevention of tissutal aging phenomena, particularly of the skin, which the recent biochemical knowledge ascribe, inter alia, to the action of free radicals, responsible of the structural alteration of the membrane lipids.

The development of biocompatible, hydrosoluble formulations is of particular interest for a better bioavailability of ubidecarenone-10 both in the pharmaceutical and cosmetic use.

The present invention concerns the development of a system able to carry in aqueous media the ubidecarenones, thanks to the interaction with amphipatic ions of general formula $RNH—CH_2—CH_2—SO_3$, wherein R is an acyl radical having more than 5 carbon atoms, preferably a natural fatty acid of the normal, iso, anteiso series or cycloalkyl, saturated or unsaturated having from 8 to 26 carbon atoms. This class of amphipatic molecules is surprisingly able to carry the ubidecarenones in water, in the form of micellar and/or liposomial aggregates, even using an equimolar ratio of the two compounds.

A molar excess of the amphipatic solubilizing species is preferably used, from 2 to 4 times higher than the vitamin, said conditions granting a better and faster solubilization.

The preparation of hydrosoluble ubidecarenones may be carried out in different ways, for instance by sonicating an aqueous solution of the amphipatic species, to which the ubidecarenone is added or preferably by dispersing in water, under vigorous stirring, a mixture of ubidecarenone and N-acyl-2-amino-ethanesulphonate, prepared by evaporation of a solution of the two compounds in an organic solvent, in which both are soluble.

The micellar and/or liposomial systems so prepared are stable over long periods of time, even at extremely low or high environmental temperatures, that may be moreover lyophilized, yielding generally materials of waxy consistency, easily soluble in water by simple stirring.

The advantages attained by the invention in the cosmetic use are:

(a) the possibility of using hydrating, non-oily preparations, also in combination with other active principles;

(b) a good absorption of the active principle by the derma, because of its micellar and/or liposomial organization;

(c) a good tolerability even in prolonged treatments;

(d) the possibility of sterilizing by filtration the preparation thanks to its reduced size and to the stability of the micellar and/or liposomial aggregates;

(e) the possibility of modulating the characteristics of the preparation by changing the acyl residues of the solubilizing agent.

The invention provides therefore cosmetic compositions containing as the active principle compounds of ubidecarenone and N-acyl-2-amino-ethanesulphonates optionally in admixture with conventional cosmetic excipients.

The compositions of ubidecarenone and N-acyl-2-aminoethansulphonates find specific use in the cosmetic field in the prevention of tissutal aging phenomena. Said action exerted by ubidecarenone is to be ascribed to a specific protective mechanism from the peroxidative phenomena on the double bonds of the membrane unsaturated fatty acids and to the specific roles of this vitamin in the cellular respiration processes.

The procedures generally described in the present invention, because of their simplicity or limited cost, are easily suited to the development of preparative processes on the industrial scale.

The cosmetic preparations of the invention are prepared according to well-known methods and using conventional excipients such as those described in "Remington's Pharmaceutical Sciences", Hack Pub. Co., N.Y., USA. Examples of said preparation are creams, lotions, also in form of sprays, containing from 0.5 to 10% by weight of an hydrosoluble ubiquinone derivative, particularly of ubidecarenone-10.

Other cosmetically active substances may be used in combination with the ubidecarenone derivatives of the invention.

The compositions are applied to the skin in the usual amounts in order to achieve the desired cosmetic effects, for instance anti-aging and hydrating effects, cellular regeneration, stimulation of the hair growth, protection from damages induced by UV radiations, anti-wrinkles and anti-scurf effects.

The following examples illustrate the preparation of different kinds of soluble ubidecarenones. They necessarily concern only some of the numerous possibilities which can be envisaged and, without any limitative character, they only define the scope of the invention.

EXAMPLE 1

62.5 g of 2-amino-ethansulphonate, suspended in 500 ml of anhydrous dimethylformamide, were reacted at 70° C. for 10 hours with 410 g of oleic anhydride, in the presence of 0.5 g of dimethylaminopyridine as a catalyst.

After evaporation of the solvent under vacuo, the oily residue was repeatedly triturated in ethyl ether. 190 g of N-oleyl-2-amino-ethansulphonate as a waxy, white solid, were obtained.

The $^2H$-NMR spectrum in $CDCl_3$ shows the signal of the acyl moiety, in the correct integration ratio, at $\delta$ 5.3; 2.4; 1.9; I.r.: 1.3 and 0.9 and those of 2-aminoethanesulphonate at $\delta$ 3.7 and 4.6.

86.2 g of ubidecarenone-10 were added to 81 g of N-oleyl-2-aminoethansulphonate, dissolved in 2.8 liters of water.

The obtained biphasic system, after sonication, yields an homogeneous phase of micellar and/or liposomial kind, stable in time and to the environmental parameters. For instance, freezing of the solution or its heating do not change the chemico-physical state of the dispersed supermolecular aggregates.

EXAMPLE 2

87.5 g of 2-amino-ethanesulphonate, suspended in 500 ml of anhydrous pyridine, were reacted at 50° C. for 10 hours with 311 g of linolenic acid chloride.

After evaporation of the solvent under vacuo, the oily residue was first triturated in ethyl ether and then, dissolved in water, was dialyzed against water. After lyophilization 255 g of N-linoleyl-2-amino-ethanesulphonate as a white, waxy solid, were obtained. The $H^1$-NMR spectrum recorded in $CDCl_3$ shows, in the correct integration ratios the signals of the acyl moiety at δ 5.3; 2.8; 2.4; 1.9; 1.6; 1.3; 0.9 and those of 2-amino-ethanesulphonate at 3.7 and 4.6.

172 g of ubidecarenone-10 and 321 g of N-linoleyl-2-amino-ethanesulphonate were dissolved in 2 l of $CHCl_3$.

After evaporation of the solvent under vacuum, 3.4 liters of water were added under vigorous stirring. An homogeneous system, yellow-orange in colour, of micellar and/or liposomial kind, stable in time and to the environmental parameters was obtained.

EXAMPLE 3

43.1 g of ubidecarenone-10 and 64.2 g of arachidonyl-2-amino-ethanesulphonate were dissolved in 1 l of $CHCl_3$.

After removal of the solvent, 2 l of water were added under vigorous stirring, till the formation of a stable micellar and/or liposomial system. After freezing and lyophilization of the solution a waxy compound orange in colour, readily soluble in the presence of water, was obtained.

We claim:

1. A ubidecarenone derivative formed by the addition of an N-acyl-2-amino-ethane-sulphonate to ubidecerenone, the acyl radical of said sulphonate having more than 5 carbon atoms and said ubidecarenone and said sulphonate being at least in equimolar ratio.

2. A ubidecarenone derivative according to claim 1 in which the acyl radical is derived from a fatty acid of 8-26 carbon atoms.

3. A ubidecarenone derivative according to claim 1 in which the ubidecarenone is 2,3-dimethoxy-5-methyl-6-decaprenyl-1-4-benzoquinone, the acyl radical is oleyl or linoleyl, and the sulphonate is used in a 2-4 molar excess to the ubidecarenone.

4. A cosmetic preparation for topical use in skin treatment for tissue aging, which comprises a homogeneous aqueous phase of lipsome and/or micelle containing as the principal active ingredient an effective amount of the ubidecarenone derivative according to claim 3.

5. A cosmetic preparation for topical use in skin treatment for tissue aging, which comprises a homogeneous aqueous phase of lipsome and/or micelle containing as the principal active ingredient an effective amount of the ubidecarenone derivative of claim 4.

6. A cosmetic preparation for topical use in skin treatment for tissue aging, which comprises a homogeneous aqueous phase of lipsome and/or micelle containing as the principal active ingredient an effective amount of the ubidecarenone derivative of claim 5.

* * * * *